United States Patent
Bardet et al.

(10) Patent No.: US 6,759,543 B2
(45) Date of Patent: Jul. 6, 2004

(54) PROCESS FOR EXTRACTING UNSAPONIFIABLE COMPONENTS OF VEGETABLE OILS BY MEANS OF 1-CHLOROBUTANE

(75) Inventors: Sandrine Bardet, Asnieres/Nouere (FR); Jacques Legrand, Neuilly-sur-Eure (FR); Antoine Piccirilli, Versailles (FR)

(73) Assignee: Laboratoires Expanscience, Courbevoie Cedex (FR)

( * ) Notice: Subject to any disclaimer, the term of this patent is extended or adjusted under 35 U.S.C. 154(b) by 0 days.

(21) Appl. No.: 10/181,056

(22) PCT Filed: Jan. 9, 2001

(86) PCT No.: PCT/FR01/00054

§ 371 (c)(1),
(2), (4) Date: Jul. 12, 2002

(87) PCT Pub. No.: WO01/51596

PCT Pub. Date: Jul. 19, 2001

(65) Prior Publication Data

US 2003/0130532 A1 Jul. 10, 2003

(30) Foreign Application Priority Data

Dec. 1, 2000 (FR) .......................................... 00 00333

(51) Int. Cl.$^7$ ................................................. C11B 7/00
(52) U.S. Cl. ....................... 554/210; 554/206; 554/208; 554/209
(58) Field of Search ................................. 554/210, 206, 554/208, 209

(56) References Cited

U.S. PATENT DOCUMENTS 2,542,119 A 2/1951 Cole

FOREIGN PATENT DOCUMENTS

| FR | 2 678 632 | 1/1993 |
| FR | 2 762 512 | 10/1998 |
| GB | 1 142 804 | 2/1969 |
| GB | 1142804 | * 2/1969 |

* cited by examiner

*Primary Examiner*—Deborah Carr
(74) *Attorney, Agent, or Firm*—Foley & Lardner

(57) ABSTRACT

The invention concerns a method for extracting usaponifiable matters from a vegetable oil comprising at least a saponification step whereby the oil is transformed into a hydro alcoholic solution, a step for extracting the hydro alcoholic solution with a organic solvent such as chloro-1-butane, preferably the treated vegetable oil is avocado or soya oil.

11 Claims, No Drawings

PROCESS FOR EXTRACTING UNSAPONIFIABLE COMPONENTS OF VEGETABLE OILS BY MEANS OF 1-CHLOROBUTANE

The present invention relates to a process for extracting the unsaponifiable components of vegetable oils and to pharmaceutical or cosmetic compositions containing the unsaponifiable components thus obtained, and to the use of these compounds for the manufacture of a medicament, in a method of cosmetic treatment and as a food additive.

Unsaponifiable compounds constitute the fraction of a fatty substance which, after prolonged action of an alkaline base, remains insoluble in water and can be extracted with an organic solvent.

Five main groups of substances are present in most unsaponifiable components of vegetable oils: saturated or unsaturated hydrocarbons, aliphatic or terpenic alcohols, sterols, tocopherols and carotenoid and xanthophilic pigments.

Unsaponifiable compounds are sought after for their pharmacological, cosmetic and nutritional properties.

The usual processes for producing unsaponifiable components of vegetable oils comprise a step of saponification of the fats and extraction of the target products (the unsaponifiable component) with an organic solvent. Generally, the solvents most commonly used are solvents for oils, such as alkanes (hexane, heptane and the like) and chlorinated solvents (dichloroethane, trichloroethane, carbon tetrachloride and the like).

Among the latter, dichloroethane constitutes the best candidate by virtue of its effective extraction yield and its intrinsic selectivity. The unsaponifiable components are indeed composed of numerous substituents which need to be extracted completely and with a maximum yield.

However, from the industrial point of view, the toxicity of the solvent used as well as its chemical stability must be taken into account. In this regard, dichloroethane (DCE) has two major disadvantages: DCE is indeed classified among the most toxic solvents, and has, moreover, a detrimental impact on the environment. In addition, DCE is partially degraded in basic medium (case of soapy saponification solutions).

The problem posed by the present invention is to choose an extraction solvent which is less toxic and chemically more stable than dichloroethane and which makes it possible to extract the unsaponifiable components with a yield and a selectivity which are at least comparable to the yields and selectivities obtained using dichloroethane, it being possible for this solvent also to be used in a crystallization process.

The subject of the present invention is thus a process for extracting the unsaponifiable fraction contained in a vegetable oil or of a coproduct of the vegetable oil refining industry such as the unchanged materials from deodorization, comprising at least:

A) a step during which the said oil is converted to an aqueous-alcoholic solution which is preferably a step chosen from the group consisting of saponifications and esterifications, B) a step of extraction of the aqueous-alcoholic solution during which the fatty fraction is separated from the unsaponifiable fraction chosen from the group consisting of liquid-liquid extractions and distillations, C) optionally, a step of purification of the unsaponifiable component chosen from the group consisting of crystallizations and liquid-liquid extractions, such as at least one step among the liquid-liquid extractions of step B, the crystallizations of step C or the liquid-liquid extractions of step C is carried out using 1-chlorobutane.

The process according to the present invention makes it possible to extract an unsaponifiable fraction contained in a vegetable oil; it also makes it possible to extract a coproduct of the vegetable oil refining industry, such as for example the unchanged materials from deodorization, also called deodistillates, which are produced during the refining of vegetable oils.

The fatty acids and the partial glycerides present in the deodistillates may indeed be saponified or esterified with a light alcohol, with the aim of separating the fatty fraction from the unsaponifiable fraction, either by liquid-liquid extraction or vacuum distillation. Finally, the purification of the unsaponifiable component or of the active fractions separated, most often the tocopherols (vitamin E) and the sterols, involves in particular steps of crystallization from an organic solvent or of liquid-liquid extraction.

The subject of the present invention is also a process for extracting the unsaponifiable fraction contained in a vegetable oil, comprising at least:

A) a saponification step by which the said oil is converted to an aqueous-alcoholic solution, B) a step of extraction of the aqueous-alcoholic solution with an organic solvent such that the organic solvent is 1-chlorobutane; preferably, the vegetable oil treated is an avocado oil or soybean oil.

More particularly, the process for extracting the unsaponifiable fraction of an avocado oil according to the present invention is such that a countercurrent extraction of the aqueous-alcoholic solution is carried out by means of 1-chlorobutane, the (volume/volume) v/v 1-chlorobutane/aqueous-alcoholic solution ratio being between 0.5 and 5, preferably between 0.9 and 1.2 and more preferably still about 1.

More particularly, the process for extracting the unsaponifiable fraction of a soybean oil according to the present invention is such that a countercurrent extraction of the aqueous-alcoholic solution is carried out by means of 1-chlorobutane, the (volume/volume) v/v 1-chlorobutane/aqueous-alcoholic solution ratio being between 0.5 and 5, preferably between 0.9 and 1.5 and more preferably still about 1.3.

The subject of the present invention is also a process for extracting the unsaponifiable fraction of a coproduct of the vegetable oil refining industry, such that this coproduct is a deodistillate of a vegetable oil, the said process comprising at least:

a saponification step by which the deodistillate is converted to an aqueous-alcoholic solution, a step of countercurrent extraction of the aqueous-alcoholic solution by means of 1-chlorobutane, a step of crystallization of the sterols and/or of the triterpenic alcohols, a step of isolation of an active compound such as tocopherols, tocotrienols, squalene, carotenes, sesamin or sesamolin, which step is chosen from the group consisting of extractions, preferably by means of 1-chlorobutane, and distillations.

The subject of the present invention is also the unsaponifiable fraction obtained by the extraction process according to the present invention.

Comparison of the contents of unsaponifiable components of various vegetable oils: soybean, cotton, coconut, olive and avocado, shows that the avocado oil obtained by extraction according to various known processes comprises a particularly high level of unsaponifiable components. Typically, the contents obtained range from 2 to 7% of unsaponifiable components in avocado oil against 0.5% in coconut oil, 1% in soybean oil, 1% in olive oil. The unsaponifiable component of avocado may be prepared by extraction from avocado oil.

The process for extracting the unsaponifiable components of an avocado oil may be carried out in the following manner.

According to a method known to persons skilled in the art:
either the fresh pulp is pressed in the presence of a third fibrous substance absorbing water such as coffee parchment in a cage press, and then the emulsion of oil and water obtained is separated by decantation and/or centrifugation;
or the fresh pulp is ground and brought into contact with a suitable organic solvent (for example a methanol-chloroform mixture) and then the oil is recovered by evaporation of the solvent.

Several processes have been described in the prior art for extracting the unsaponifiable fraction of a vegetable oil.

There may be mentioned in particular the process for preparing the unsaponifiable component of avocado oil as described and claimed in patent FR-2,678,632 in the name of Pharmascience Laboratories. This process makes it possible to obtain an unsaponifiable component of avocado rich in fraction H by comparison with the conventional processes for preparing the unsaponifiable component of avocado.

Thus, the unsaponifiable component of avocado oil used according to the invention may be obtained from fresh fruit but, preferably, the unsaponifiable component of avocado is prepared from fruit which has been previously heat-treated before the extraction of the oil and the saponification, as described in patent FR-2,678,632. This heat treatment consists in a controlled drying of the fruit, preferably fresh fruit, for at least four hours, advantageously at least 10 hours, preferably between about 24 and about 48 hours, at a temperature preferably of at least about 80° C. and preferably between 80 and about 120° C.

There may also be mentioned the process for preparing the unsaponifiable component of soybean oil, obtained from an unsaponifiable concentrate of soybean oil. The said unsaponifiable concentrate is prepared by molecular distillation according to a process as described for lupin oil in patent application FR-2,762,512, but adapted for soybean oil. In this process, the soybean oil is distilled in a molecular distillation apparatus of the centrifugal or scraped-film type, at a temperature of between about 210 and 250° C. and under a high vacuum of between 0.01 and 0.001 millimetres of mercury (that is 0.13 to 1.3 Pa). The distillate obtained has a content of unsaponifiable component of between 5 and 40% by weight and therefore constitutes an unsaponifiable concentrate of soybean oil.

The concentrate is then saponified with a base such as potassium hydroxide or sodium hydroxide in an alcoholic, preferably ethanolic, medium. It is then subjected to one or more extractions with 1-chlorobutane.

The extraction solution obtained is then preferably centrifuged, filtered and then washed with water in order to remove residual traces of alkalinity.

The extraction solvent is carefully evaporated in order to recover the unsaponifiable component. It is of course also possible to envisage additional operations known to persons skilled in the art, such as a deodorization step.

Finally, before its saponification, oil may be enriched beforehand in unsaponifiable component by separating a majority of the constituents from the unsaponifiable component which is recovered in a concentrate. Various methods can be used: cold crystallization, liquid-liquid extraction, molecular distillation.

The preliminary concentration of the oil in unsaponifiable component makes it possible to reduce the consumption of oil during the saponification. Molecular distillation is particularly preferred, being preferably carried out at a temperature of between about 180 and about 230° C., while a pressure of between $10^{-3}$ and $10^{-2}$ mmHg, and preferably of the order of $10^{-3}$ mmHg, is maintained. The concentration of unsaponifiable components of the distillate may be up to 60%.

The subject of the present invention is also a cosmetic composition comprising at least one unsaponifiable fraction contained in a vegetable oil and a cosmetically acceptable excipient, a pharmaceutical composition or a composition as a medicament comprising at least one unsaponifiable fraction contained in a vegetable oil and a pharmaceutically acceptable excipient and a dietary composition comprising at least one unsaponifiable fraction contained in a vegetable oil.

The present invention also relates to a process of cosmetic treatment such that the cosmetic composition according to the invention is applied topically and also to the use of an unsaponifiable component of a vegetable oil obtained according to the present invention for the manufacture of a medicament.

By way of examples illustrating the present invention, two series of experiments were successively carried out.

EXAMPLE I

First Series of Extractions (In a Separating Funnel)

Before extraction of the unsaponifiable component, the concentrate of the oil considered (avocado or soybean) is saponified in a first step, this concentrate being obtained beforehand by molecular distillation of the oil.

After saponification, an aqueous-alcoholic solution, called AAS, containing the unsaponifiable component in solution, is obtained. This unsaponifiable component is then extracted with an organic solvent: DCE chosen as reference and 1-chlorobutane (1CB).

The mass of concentrate to be saponified (plus optionally the diluting oil for avocado) is accurately weighed in a 100 ml round-bottomed flask equipped with a condenser. The ethyl alcohol, the potassium hydroxide and a few granules of boiling chips are then added and the mixture is heated under reflux for 4 hours. After cooling, the reaction medium is diluted with demineralized water.

The extraction is carried out in a separating funnel. The organic phases are then combined and washed with tap water to neutrality (phenolphthalein test).

The solvent phase obtained is then dried over anhydrous sodium sulphate (3 g). After filtration, the solvent is evaporated in a rotary evaporator. The unsaponifiable component recovered is finally weighed and then stored under nitrogen, before GC (gas chromatography) and HPLC (high-performance liquid chromatography) analysis.

Results

After optimization of the extraction conditions (Tables 1 and 2), the results obtained are assembled in Tables 3 and 4.

TABLE 1

Conditions for saponification and extraction of the avocado concentrates

|  | DCE | 1CB |
| --- | --- | --- |
| Avocado concentrate (g) | 10 | 10 |
| Potassium hydroxide (g) | 5 | 5 |
| Alcohol (ml) | 24 | 44 |
| Dilution water (ml) | 35 | 30 |

TABLE 1-continued

Conditions for saponification and extraction of the avocado concentrates

|  | DCE | 1CB |
| --- | --- | --- |
| Extraction solvent | 5 × 35 ml | 7 × 50 ml |
| Washing | 5 × 100 ml | 6 × 50 ml |

TABLE 2

Conditions for saponification and extraction of the soybean concentrates

|  | DCE | 1CB |
| --- | --- | --- |
| Soybean concentrate (g) | 10 | 10 |
| Potassium hydroxide (g) | 4 | 4 |
| Alcohol (ml) | 24 | 44 |
| Dilution water (ml) | 35 | 25 |
| Extraction solvent | 5 × 35 ml | 6 × 50 ml |
| Washing | 5 × 100 ml | 6 × 50 ml |

TABLE 3

Analyses and yields of extraction of the unsaponifiable components of avocado

| Unsaponifiable component analysis (%) (1) | DCE | 1CB |
| --- | --- | --- |
| Furanic compounds | 70.0 | 67.2 |
| Polyhydroxylated fatty alcohols | 15.7 | 16.6 |
| Hydrocarbons | 1.0 | 0.5 |
| Squalene | 1.5 | 1.3 |
| Tocopherols | Traces | Traces |
| Sterols | 4.7 | 3.9 |
| Others | 7.1 | 10.5 |
| Extraction yields (%) (1) | 41.7 | 46.3 |

(1) Percentages expressed relative to the concentrate which is the composition available before saponification.

TABLE 4

Analyses and yields of extraction of the unsaponifiable components of soybean

| Unsaponifiable component analysis (%) (1) | DCE | 1CB |
| --- | --- | --- |
| Hydrocarbons | 0.8 | 0.7 |
| Squalene | 9.8 | 11.6 |
| Tocopherols | 28.4 | 21.4 |
| Sterols | 60.4 | 66.3 |
| Extraction yields (%) (1) | 36.4 | 34.8 |

(1) Percentages expressed relative to the concentrate which is the composition available before saponification.

These results (Table 3) show that the unsaponifiable components of avocado are extracted in the presence of 1-chlorobutane with yields greater than those obtained with DCE. Moreover, the composition of the unsaponifiable components is similar to the reference (unsaponifiable components extracted with DCE).

The results in Table 4 show that, with 1-chlorobutane, the unsaponifiable components of soybean are extracted with a yield which is very slightly lower than with DCE and that the composition of the unsaponifiable components is very similar to the reference (unsaponifiable component extracted with DCE).

In conclusion, 1-chlorobutane is found to be an excellent candidate for replacing the conventional solvents for unsaponifiable components.

EXAMPLE II

Second Series of Extractions

These trials were carried out in a micropilot series of mixer-settlers of the Robatel brand, whose operation allows extrapolation of the results to an industrial extractor of the series of mixer-settlers type or of the countercurrent pulsed column type.

The solution to be extracted is an aqueous-alcoholic solution (AAS), obtained from a saponification reaction. Indeed, before carrying out the liquid-liquid extraction of the unsaponifiable component, the process for producing this same unsaponifiable component comprises two preliminary steps. The first consists in concentrating the unsaponifiable fraction by molecular distillation of the crude or refined oil. The second relates to the saponification of the concentrate of unsaponifiable component obtained, in the presence of potassium hydroxide in alcoholic medium. At the end of the reaction, the mixture is diluted with demineralized water and then sent into a pulsed column so as to be subjected to the extractive action of an organic solvent, capable of bringing about the liquid-liquid extraction of the unsaponifiable component.

1) Preparation of the Aqueous-Alcoholic Solution to be Extracted (AAS)

The required quantities of aqueous potassium hydroxide, alcohol and fatty substance to be saponified are successively introduced into a 100-litre jacketed reactor (steam heating) of the Grignard type, equipped with a mechanical stirrer and fitted with a condenser. The mixture is heated, with constant stirring, to the reflux temperature of ethanol (70–80° C.) and then maintained at this temperature for 3.5 hours. After reaction, the mixture is cooled to 30° C. and then diluted by addition of the required quantity of demineralized dilution water. The aqueous-alcoholic solution obtained is then sent into the series of mixer-settlers so as to be subjected to the liquid-liquid extraction step.

TABLE 5

Compositions of the saponification media

| REAGENTS | Saponification of an avocado concentrate (1) | Saponification of a soybean concentrate (1) |
| --- | --- | --- |
| Concentrate* | 10 | 10 |
| Ethyl alcohol* | 25 | 16 |
| Aqueous potassium hydroxide at 50%* | 5 | 4 |
| Final dilution water* | 48 | 30 |

(1) Concentrate obtained by molecular distillation of the starting oil
*In kilograms 2) Liquid-Liquid Extraction of the Unsaponifiable Components The liquid-liquid extraction of the unsaponifiable components of avocado and soybean is carried out in a series of mixer-settlers of the Robatel type. The extractor is fed with the avocado or soybean aqueous-alcoholic solution, AAS, and then countercurrentwise with the solvent used (dichloroethane or 1-chlorobutane). To check that the extractor is in the stationary mode, the flow rates are recorded every 15 minutes. When the operating mode is reached, samples of each phase (extract and raffinate) are collected after 60 minutes of operation. The analysis of the phases collected is carried out continuously.

The quantity of unsaponifiable component extracted relative to the aqueous-alcoholic solution obtained is determined in the following manner:

$$\% \text{ unsaponifiable component extracted} = 100 \times (D_{EX} \times X_{EX})/(D_{AAS} \times X_{AAS})$$

with:

$D_{EX}$: mass flow rate of the extract $D_{AAS}$: mass flow rate of the aqueous-alcoholic solution $X_{EX}$: mass titre of the extract in %

$X_{AAS}$: mass titre of the aqueous-alcoholic solution in %

3) Results 3.1 Extraction of the Unsaponifiable Components of Avocado

Comparative Extraction with DCE (dichloroethane) and with 1-chlorobutane (1CB)

TABLE 6

Comparison of the extractive properties of Dichloroethane (DCE) and 1-Chlorobutane (1CB)

| SOLVENT | SOLVENT/ASS RATIO | UNSAPONIFIABLE COMPONENT EXTRACTED (%) |
|---|---|---|
| DCE | 1.0 | 95.0 |
| 1CB | 1.0 | 97.7 |

COMPOSITION OF THE UNSAPONIFIABLE COMPONENT EXTRACTED

| SOLVENT | Fraction H | Fraction I | Sterols | Squalene | Fatty acids | Others |
|---|---|---|---|---|---|---|
| DCE | 67.6 | 8.0 | 4.4 | 1.3 | 0.4 | 18.3 |
| 1CB | 75.8 | 1.9 | 4.1 | 1.4 | 0.4 | 16.4 |

Fraction H represents the furans in avocado, and more particularly the compounds of formula:

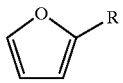

in which R is a linear $C_{11}$–$C_{19}$, preferably $C_{13}$–$C_{17}$, hydrocarbon chain which is saturated or which comprises one or more ethylenic or acetylenic unsaturations, and fraction I represents the polyhydroxylated fatty alcohols of avocado and more particularly the expression "polyhydroxylated fatty alcohols of avocado" is understood to mean polyols in the form of a principal linear $C_{17}$–$C_{21}$, hydrocarbon chain which is saturated or which comprises one or more ethylenic or acetylenic unsaturations, and which comprises at least two hydroxyl groups predominantly situated on one portion of the principle chain, the other portion of this principal chain thus constituting the "fatty" chain (hydrophobic portion) of the polyol.

These results show that:

1-Chlorobutane is found to be an excellent solvent for extraction of the unsaponifiable components of avocado.

The quantity of unsaponifiable component extracted is at least equal to, or even greater than that for dichloroethane which is recognized as an excellent solvent for extraction of the unsaponifiable components.

From the point of view of their composition, the unsaponifiable components extracted are very similar. However, 1-chlorobutane is more selective for fraction H, at the expense of fraction I (polyhydroxylated fatty alcohols of avocado).

Influence of the Solvent/AAS Ratio

TABLE 9

Influence of the 1-Chlorobutane/Aqueous-alcoholic solution (AAS) ratio

| 1-Chlorobutane/ AAS mass ratio | DCE/AAS = 1 (1) | 0.8 | 0.9 | 1.2 |
|---|---|---|---|---|
| Unsaponifiable component extracted (%) | 95.5 | 88.6 | 94.8 | 98.7 |
| Fraction H (%) | 67.6 | 74.4 | 72.4 | 71.3 |
| Fraction I (%) | 8.0 | 1.2 | 2.0 | 2.1 |
| Sterols (%) | 4.4 | 3.1 | 3.7 | 3.9 |
| Fatty acids (%) | 0.4 | 0.4 | 0.3 | 0.5 |
| Others (%) | 19.6 | 20.9 | 21.6 | 22.2 |

(1) Dichloroethane: reference solvent

Conclusions:

The quantity of unsaponifiable component extracted tends to increase with the chlorobutane/AAS ratio.

The optimum ratio is between 0.9 and 1.2.

3.2 Extraction of the Unsaponifiable Components of Soybean

The extraction of the unsaponifiable components of soybean requires maintaining the aqueous-alcoholic solution at a temperature of between 35° C. and 40° C.

Comparative Extraction with Dichloroethane (DCE) and with 1-Chlorobutane (1CB)

TABLE 10

Comparison of the extractive properties of Dichloroethane (DCE) and Chlorobutane (1CB)

| SOLVENT | SOLVENT/AAS RATIO | UNSAPONIFIABLE COMPONENT EXTRACTED (%) |
|---|---|---|
| DCE | 1.0 | 90.7 |
| 1CB | 1.3 | 97.7 |

COMPOSITION OF THE UNSAPONIFIABLE COMPONENT EXTRACTED

| SOLVENT | Sterols | Tocopherols | Hydrocarbons | Squalene |
|---|---|---|---|---|
| DCE | 65.5 | 20.8 | 1.3 | 12.4 |
| 1CB | 62.0 | 22.5 | 1.0 | 14.5 |

The results show that:

1-Chlorobutane is found to be an excellent solvent for extraction of the unsaponifiable components of soybean.

The quantity of unsaponifiable component extracted is greater than that for dichloroethane which is recognized as an excellent solvent for extraction of the unsaponifiable components.

From the point of view of their composition, the unsaponifiable components extracted are very similar. This solvent is therefore perfectly suitable for the extraction of the unsaponifiable components of conventional vegetable oils.

EXAMPLE III

Extraction of the Upgradable Unsaponifiable Fractions of a Distillate of Soybean Oil

EXAMPLE III-1

In a Grignard-type reactor, 100 kg of deodistillate of soybean oil are saponified under reflux in the presence of 40 kg of aqueous potassium hydroxide (at 50%) and of 200 litres of ethyl alcohol. After saponification, the reaction mixture is diluted by addition of 300 kg of demineralized water and then sent into a countercurrent pulsed extraction column. The solvent used is 1-chlorobutane (solvent/aqueous-alcoholic solution ratio=1). After extraction, the organic phase is washed in a washing column which is continuously supplied with demineralized water. The 1-chlorobutane, the extraction solvent, is finally separated from the crude unsaponifiable component in a falling-film-type evaporator.

After evaporation, the crude unsaponifiable component obtained is dissolved in the hot state in 65 litres of ethanol. The mixture is then cooled, with slow mechanical stirring, from 70° C. to 15° C. and maintained for two and a half hours at this temperature. The crystallization of the sterols starts at 45° C. After rapid draining over a Büchner funnel, a series of washings of the crystallized sterols is carried out with 50% ethanol and then with demineralized water. The filtration cake, consisting of the extracted sterols, is finally dried in a ventilated oven at 80° C. for 12 hours. 9.7 kg of sterols are thus obtained whose purity is close to 98%.

The ethanolic phase recovered is then evaporated off. The partially sterol-free unsaponifiable component obtained is then subjected to a molecular distillation step at 120° C., under a vacuum of $10^{-3}$ mm of mercury. 11.8 kg of distillate (light fraction) composed of 90% of hydrocarbons are recovered. The residue (heavy fraction) has a tocopherol content of close to 50%.

EXAMPLE III-2

100 kg of deodistillate of soybean oil are distilled at 130° C. and under a vacuum of $10^{-3}$ mm of mercury. A light fraction (41.5 kg) essentially composed of hydrocarbons and fatty acids as well as a heavy fraction (58.5 kg) rich in sterols and tocopherols are recovered. The latter fraction is then saponified in a manner identical to Example 1, in the presence of 90 litres of ethanol and 15 kg of 50% aqueous potassium hydroxide.

The mixture obtained is then cooled, with slow mechanical stirring, from 80° C. to 15° C. and maintained at this temperature for 1 hour. The crystallization of the sterols starts at 45° C. Rapid draining over a Büchner funnel and then a series of washings with 50% ethanol and with demineralized water are then carried out. The filtration cake, consisting of the extracted sterols, is finally dried in a ventilated oven at 80° C. for 12 hours. 9.1 kg of sterols whose purity is greater than 95% are thus obtained.

The filtrate recovered is then diluted with 60 litres of demineralized water and then sent into a countercurrent pulsed extraction column. The solvent used is 1-chlorobutane (solvent/aqueous-alcoholic solution ratio=1). After extraction, the organic phase is washed in a washing column which is continuously supplied with demineralized water. The 1-chlorobutane, the extraction solvent, is finally separated from the residual unsaponifiable fraction in a falling-film-type evaporator. The fraction obtained (19.3 kg) is highly enriched in tocopherols (45%).

These results show that 1-chlorobutane is a good solvent for extraction of the unsaponifiable fraction of a deodistillate, in particular of soybean, and makes it possible to selectively extract one of the active fractions of this unsaponifiable component, such as sterols or tocopherols.

What is claimed is:

1. Process for extracting of the unsaponifiable fraction contained in a vegetable oil or of a coproduct of the vegetable oil refining industry, comprising at least:

A) a step during which the said oil is converted to an aqueous-alcoholic solution which is a step chosen from the group consisting of saponifications and esterifications, B) a step of extraction of the aqueous-alcoholic solution during which the fatty fraction is separated from the unsaponifiable fraction chosen from the group consisting of liquid-liquid extractions and distillations, C) a step of purification of fraction the unsaponifiable component chosen from the group consisting of crystallizations and liquid-liquid extractions, characterized in that at least one step among the liquid-liquid extractions of step B, the crystallizations of step C or the liquid-liquid extractions of step C is carried out using 1-chlorobutane.

2. Process for extracting the unsaponifiable fraction contained in a vegetable oil according to claim 1, comprising at least:

A) a saponification step by which the said oil is converted to an aqueous-alcoholic solution, B) a step of extraction of the aqueous-alcoholic solution with an organic solvent, characterized in that the organic solvent is 1-chlorobutane.

3. Process for extracting the unsaponifiable fraction contained in a vegetable oil according to claim 2, characterized in that the vegetable oil is an avocado oil.

4. Process for extracting the unsaponifiable fraction contained in a vegetable oil according to claim 2, characterized in that the vegetable oil is a soybean oil.

5. Process for extracting the unsaponifiable fraction contained in an avocado oil according to claim 3, characterized in that a countercurrent extraction of the aqueous-alcoholic solution is carried out by means of 1-chlorobutane, the v/v 1-chlorobutane/aqueous-alcoholic solution ratio being between 0.5 and 5.

6. Process for extracting the unsaponifiable fraction contained in an avocado oil according to claim 5, characterized in that the v/v 1-chlorobutane/aqueous-alcoholic solution ratio is between 0.9 and 1.2.

7. Process for extracting the unsaponifiable fraction contained in an avocado oil according to claim 6, characterized in that the v/v 1-chlorobutane/aqueous-alcoholic solution ratio is about 1.

8. Process for extracting the unsaponifiable fraction contained in a soybean oil according to claim 4, characterized in that a countercurrent extraction of the aqueous-alcoholic solution is carried out by means of 1-chlorobutane, the (volume/volume) v/v 1-chlorobutane/aqueous-alcoholic solution ratio being between 0.5 and 5.

9. Process for extracting the unsaponifiable fraction contained in a soybean oil according to claim 8, characterized in that a countercurrent extraction of the aqueous-alcoholic solution is carried out by means of 1-chlorobutane, the (volume/volume) v/v 1-chlorobutane/aqueous-alcoholic solution ratio being between 0.9 and 1.5.

10. Process for extracting the unsaponifiable fraction according to claim 9, characterized in that a countercurrent extraction of the aqueous-alcoholic solution is carried out by means of 1-chlorobutane, the (volume/volume) v/v 1-chlorobutane/aqueous-alcoholic solution ratio being about 1.3.

11. Process for extracting the unsaponifiable fraction of a coproduct of the vegetable oil refining industry, characterized in that this coproduct is a deodistillate of a vegetable oil, the said process comprising at least:
- a saponification step by which the deodistillate is converted to an aqueous-alcoholic solution,
- a step of countercurrent extraction of the aqueous-alcoholic solution by means of 1-chlorobutane,
- a step of crystallization of the sterols and/or of the triterpenic alcohols,
- a step of isolation of an active compound such as tocopherols, tocotrienols, squalene, carotenes, sesamin or sesamolin, which step is chosen from the group consisting of extractions, by means of 1-chlorobutane, and distillations.

* * * * *

UNITED STATES PATENT AND TRADEMARK OFFICE
CERTIFICATE OF CORRECTION

| | | |
|---|---|---|
| PATENT NO. | : 6,759,543 B2 | Page 1 of 1 |
| APPLICATION NO. | : 10/181056 | |
| DATED | : July 6, 2004 | |
| INVENTOR(S) | : Bardet et al. | |

It is certified that error appears in the above-identified patent and that said Letters Patent is hereby corrected as shown below:

On Title page
     (30) Foreign Application Priority Data, "December 1, 2000." should be --January 12, 2000--.

Col. 1, line 49, change "dichioroethane" to --dichloroethane--.

Col. 10, line 7, delete "which is a step chosen from the group consisting of saponifications and esterifications".

Col. 10, line 14, "C) a step of purification of fraction the unsaponifiable" should be --C) optionally, a step of purification of the unsaponifiable fraction--.

Col. 12, line 6, delete ", by means of 1-chlorobutane,".

IN THE CLAIMS (continued)
     Col. 12, line 7, after claim 11, insert the following:
--     12. Process for extracting the unsaponifiable fraction contained in a vegetable oil according to claim 1, wherein step A) is a step chosen from the group consisting of saponifications and esterifications.
     13. Process for extracting the unsaponifiable fraction of a coproduct of the vegetable oil refining industry according to claim 11, wherein the step of isolation of the active compound is an extraction by means of 1-chlorobutane.--.

Signed and Sealed this

Twentieth Day of February, 2007

JON W. DUDAS
*Director of the United States Patent and Trademark Office*